US005296497A

United States Patent [19]

Hartog et al.

[11] Patent Number: 5,296,497

[45] Date of Patent: Mar. 22, 1994

[54] 3,4-DEHYDROPIPERIDINE DERIVATIVES HAVING PSYCHOTROPIC ACTIVITY

[75] Inventors: Jan Hartog; Roelof Van Hes; Berend Olivier; Ineke Van Wijngaarden, all of Weesp, Netherlands

[73] Assignee: Duphar International Research B.V., Weesp, Netherlands

[21] Appl. No.: 968,267

[22] Filed: Oct. 30, 1992

Related U.S. Application Data

[63] Continuation-in-part of Ser. No. 522,032, May 11, 1990, abandoned.

[30] Foreign Application Priority Data

May 16, 1989 [NL] Netherlands ........................ 8901211

[51] Int. Cl.[5] ..................... A61K 31/44; C07D 211/70

[52] U.S. Cl. .................................... 514/357; 514/332; 546/262; 546/330; 546/334; 546/335; 546/337

[58] Field of Search ............... 546/337, 330, 334, 335, 546/262; 514/332, 357

[56] References Cited

U.S. PATENT DOCUMENTS

| | | | |
|---|---|---|---|
| 4,259,338 | 3/1981 | Paioni | 514/237 |
| 4,332,808 | 6/1982 | Guillaume et al. | 514/237 |
| 4,382,942 | 5/1983 | Nedelee et al. | 514/237 |
| 4,435,408 | 3/1984 | Nedelee et al. | 514/237 |
| 4,782,061 | 11/1988 | Kruse et al. | 514/237 |

OTHER PUBLICATIONS

Guillaume et al. Chem. Abstracts 95; No. 1, 7054r (1981).

Guillaume et al. Chem. Abstracts 97; No. 19, 162817b (1982).

Boissier et al. Chem. Abstracts, 99, No. 21; 169053z (1983).

*Primary Examiner*—Bernard Dentz

*Attorney, Agent, or Firm*—Stevens, Davis, Miller & Mosher

[57] ABSTRACT

The invention relates to 3,4-dehydropiperidine derivatives having psychotropic activity, which compounds are represented by the general formula 1

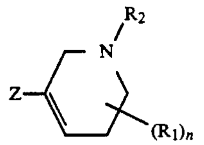

(1)

wherein

R is hydrogen or $C_1$-$C_3$ alkyl;

$R_2$ is hydrogen, an unsubstituted or substituted $C_1$-$C_{10}$ hydrocarbon group, or a group of the general formula

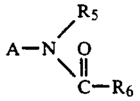

wherein A is $C_2$-$C_{10}$ alkylene, $R_5$ is hydrogen or $C_1$-$C_3$ alkyl, and $R_6$ is unsubstituted or substituted aryl or heteroaryl, hydrocarbon, substituted or unsubstituted (hetero)aralkyl, or substituted or unsubstituted heterocyclic; or wherein $R_5$ and $R_6$ together with the carbamoyl group to which they are bound constitute a heterocyclic ring system;

n has the value 1 or 2; and

Z is a heterocyclic group.

8 Claims, No Drawings

3,4-DEHYDROPIPERIDINE DERIVATIVES HAVING PSYCHOTROPIC ACTIVITY

This application is a continuation-in-part of application Ser. No. 07/522,032, filed May 11, 1990 now abandoned.

The invention relates to new 3-substituted 3,4-dehydropiperidine derivatives having psychotropic activity.

It was found that 3,4-dehydropiperidine derivates of the general formula 1

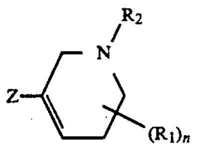
(1)

wherein $R_1$ is a hydrogen atom or an alkyl group having 1-3 carbon atoms;

$R_2$ is a hydrogen atom; a branched or non-branched, saturated or unsaturated aliphatic hydrocarbon group having 1 to 10 carbon atoms, which group may be substituted with one or more substituents selected from the group consisting of benzoyl, substituted benzoyl, hydroxy, phenyl, substituted phenyl, phenoxy, substituted phenoxy, cyano, dialkylcarbamoyl, and heteroaryl, which heteroaryl group may be substituted with phenyl, substituted phenyl, halogen, trifluoromethyl, or $C_1$-$C_4$ alkyl; or wherein $R_2$ represents a group of the general formula

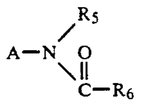

wherein:

A is a branched or non-branched alkylene group having 2 to 10 carbon atoms, $R_5$ is a hydrogen atom or alkyl group having 1 to 3 carbon atoms, and $R_6$ is an unsubstituted or substituted aryl group or heteroaryl group; a saturated or unsaturated $C_1$-$C_{10}$ aliphatic or $C_4$-$C_{10}$ cycloaliphatic hydrocarbon group; a substituted or unsubstituted aralkyl group; a substituted or unsubstituted heteroaralkyl group; or a 5 or 6 membered heterocyclic ring system which may comprise one or two additional hetero atoms selected from N, O and S and which may be substituted with one or more substituents selected from the group consisting of $C_1$-$C_4$ alkyl, oxo and halogen; or wherein $R_5$ and $R_6$ together with the carbamoyl group to which they are bound constitute a heterocyclic ring system having one or more rings, of which the carbamoyl group-containing 5 or 6 membered ring may comprise one or two additional hetero atoms selected from N, O and S and may be substituted with one or more substituents selected from the group consisting of $C_1$-$C_3$ alkyl and oxo, and in which the optionally present other rings are 3-7 membered aromatic, heterocyclic or cycloaliphatic groups which are annelated, spiro-connected or bridged with the first ring and may be substituted with one or more substituents selected from $C_1$-$C_4$ alkyl, oxo and halogen;

n has the value 1 or 2; and

Z is one of the groups of the formulas 2-19,

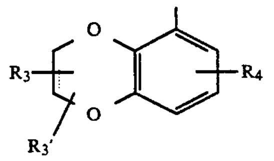
2.

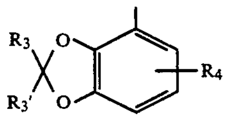
3.

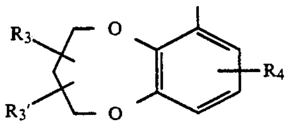
4.

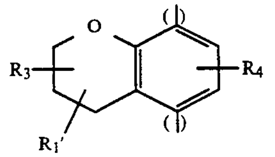
5.

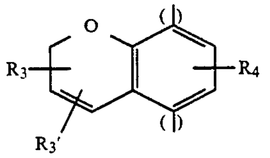
6.

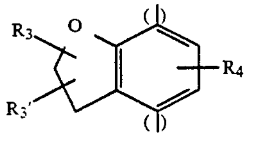
7.

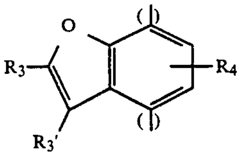
8.

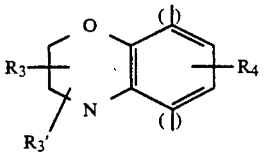
9.

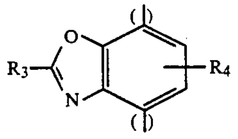
10.

-continued

11.

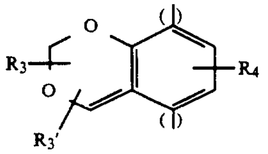

12.

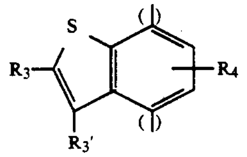

13.

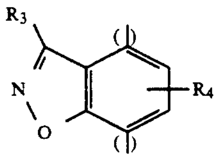

14.

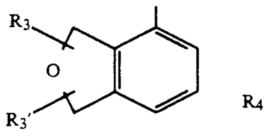

15.

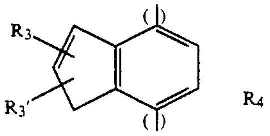

16.

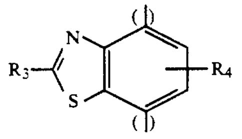

17.

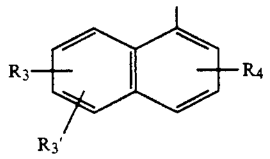

18.

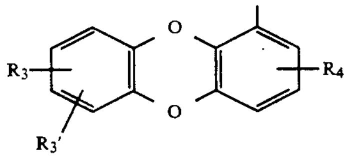

19.

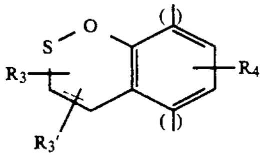

with the proviso that the groups of the formulas 5, 6, 9, 11 and 19 may be bound to the piperidine group via the position 5 or 8, the groups of the formulas 7, 8, 10, 12, 13, 15 and 16 may be bound to the piperidine group via the position 4 or 7, and the groups of the formulas 2, 3, 4, 14, 17 and 18 may be bound to the piperidine group via the indicated position, and the broken line in formulas 2 and 19 represents an optionally present double bond, in which groups $R_3$ and $R_{3'}$ may be equal or different and represent hydrogen atoms, halogen atoms, oxo functions, saturated or unsaturated $C_1$–$C_{10}$ aliphatic hydrocarbon groups, optionally esterified or etherified $C_1$–$C_6$ hydroxyalkyl groups, $C_1$–$C_4$ alkylcarbonyl groups, optionally esterified or etherified hydroxy groups, amino groups, $C_1$–$C_3$ alkylamino groups, di($C_1$–$C_3$)alkylamino groups, substituted or non-substituted aryl groups or heteroaryl groups, or aryl($C_1$–$C_3$)alkyl groups; and $R_4$ is a hydrogen atom, a halogen atom, a cyano group, a hydroxy group, a trifluoromethyl group, an alkyl group, an alkoxy group, an alkylthio group, an alkanoylamino group, an alkanoyl group, an aminocarbonyl group, an N-alkylaminocarbonyl group, an N,N-dialkylaminocarbonyl group, an alkanoyloxy group or an alkoxycarbonyl group, wherein the alkyl groups have 1 to 10 carbon atoms; have psychotropic properties.

The so-called prodrugs and acid addition salts of the compounds of formula 1 also belong to the invention. Prodrugs are to be understood to mean derivatives of these compounds, which are inactive as such but from which, after removal of an easily removable group, e.g. an ester group or an ether group, an active compound of formula I is obtained.

Examples of suitable acids with which the compounds according to the invention can form pharmaceutically acceptable salts are hydrochloric acid, sulphuric acid, phosphoric acid, nitric acid, organic acids, like citric acid, fumaric acid, tartaric acid, acetic acid, maleic acid, benzoic acid, p-toluene sulphonic acid, methane sulphonic acid and the like.

In case the compounds according to the invention comprise one or more optically active carbon atoms, both the racemates and the individual enantiomers belong to the invention. If double bonds are present in the compounds of the invention, cis-trans isomerism may occur. Isomerism may also occur in cycloaliphatic ring systems, to which substituents may be attached in different steric positions. In such cases the invention includes all possible stereoisomers.

When aryl groups or heteroaryl groups occur in the meanings of the above-mentioned symbols, they include various aromatic groups, for example, phenyl, naphthyl, thienyl, furyl, pyridyl, quinolyl, pyrimidyl, imidazolyl, pyrrolyl, oxadiazolyl, pyrazinyl, indolyl and the like. In the above-mentioned aralkyl groups or heteroaralkyl groups as meaning of $R_6$ the aryl groups and heteroaryl groups, respectively, are bound to the carbonyl function via $C_1$–$C_4$ alkyl groups. The aryl groups or heteroaryl groups may be substituted with one or more equal or different substituents. As examples of substituents to the aryl groups or heteroaryl groups may be mentioned: halogen, $C_1$–$C_4$ alkyl, $C_1$–$C_4$ alkoxy, hydroxy, esterified or etherified hydroxy, trifluoromethyl, alkylcarbonyl, cyano, $C_1$–$C_4$ alkylamino or di($C_1$–$C_4$)alkylamino. Heterocyclic groups are to be understood to mean herein not only heteroaryl groups as mentioned hereinbefore, but also non-aromatic heterocyclic groups, for example, tetrahydrofuryl, tetrahydropyranyl, piperidyl, pyrrolidinyl and the like.

By esterified and etherified hydroxy should be understood hydroxy esterified with benzoic acid, with a benzoic acid substituted as defined above, or with a straight or branched $C_2$–$C_8$ aliphatic carboxylic acid, as well as hydroxy etherified to a straight or branched, saturated or unsaturated aliphatic $C_1$-$C_8$ hydrocarbyl ether, a $C_3$-$C_6$ cycloalkyl ether or a ($C_3$-$C_6$ cycloalkyl) $C_1$-$C_4$ alkyl ether. Examples of suitable esters are: benzoate, fluorobenzoate, methylbenzoate, trifluoromethyl benzoate, methoxybenzoate, acetate, propionate, butyrate, trimethylacetate, and the like. Examples of suitable ethers are the ethyl ether, allyl ether, butyl ether, isobutyl ether, tert.-butyl ether, cyclopropyl ether, cyclopropylmethyl ether, and the like.

The compounds of the invention show an interesting affinity to serotonin-1 receptors. Compounds which show affinity to the 5-$HT_{1A}$ receptor subtype are potential anxiolytics, antidepressants, antipsychotics, memory enhancers, antihypertensives, but can also be used in vertigo and motion sickness. Compounds which display a preference for the 5-$HT_{1D}$ receptor subtype are potential antimigraine drugs.

The affinity of a compound to a certain receptor (sub)type can be determined by an in vitro receptor binding assay, by standard procedures, e.g. affinity to 5-$HT_{1A}$ receptors is measured by displacement of [$^3$H]-8-OH-DPAT according the method described by Gozlan et al. (Nature 305, 1983, 140-142).

In addition to a striking affinity to serotonin-1 receptors, the compounds of the invention show interesting psychotropic activities in animal models which inter alia are predictive for antiagressive, antipsychotic, antidepressive and/or anxiolytic properties, and for activity against migraine.

It has also been found that, dependent on the meanings of the substituents in formula 1, certain compounds moreover have hypotensive properties. These compounds may be represented by the general formula 1, wherein the substituents have the meanings mentioned hereinbefore, with the proviso that (i) the substituent $R_4$ in the group Z is a hydrogen atom or a fluorine atom and (ii) the meaning of $R_5$ in substituent $R_2$ is hydrogen.

Suitable animal models for determining such pharmacological activities are, for example, the following:

1) It is known that young rats which are separated from the mother animal and their nestling produce ultrasonic sounds, so-called pup vocalisations (see Pharm. Biochem. Behav. 24, (1986), 1263-1267). These pup vocalisations are characterised by a natural reaction and may be inhibited by means of psychotropic substances.

2) In a second animal model, use is made of the animal behaviour which is recorded after a stimulus of a more or less unpleasant nature has been induced; for example, the natural aversion to light or electric shocks. Such stimuli cause an inhibition of certain behaviour elements and lead to avoidance of the undesired situation. Compounds having a psychotropic activity prevent inhibition (see Pharm. Biochem.Behav. 13, (1980), 167-170 and Eur. J. Pharmacol. 4, (1968), 145-151).

3) It is known (see Neuropsychobiology 18, (1987), 51) that clinically effective psychotropic compounds cause a characteristic electroencephalogram (EEG).

4) It is known, e.g. from Eur. J. Pharmacol. 47, (1978), 379-391, that test animals, for example rats, take an immobile position some time after they have been forced to swim: "behaviour despair". Compounds having an antidepressive activity can extend the period of active resistance of the animals preceding this behaviour.

5) Predictive for activity against migraine is the following test model. Serotonin causes via stimulation of 5-$HT_1$-like receptors a concentration-dependent contraction of isolated strips of A. basilaris of the pig. (Naunyn Schmiedeberg's Arch. of Pharmacol. 1990, in press). This effect, that can be induced by other serotonin agonists, can be determined and is predictive for anti-migraine activity.

6) A suitable animal model for determining antihypotensive activity is described in the European patent specification 0138280 in the name of Applicants.

The compounds of formula 1 are active in the models 1), 2) and 4) and cause EEG's which show great resemblance with the EEG's caused by clinically active psychotropic compounds.

The compounds according to the invention are active in dosages which as a rule are between 0.1 and 100 mg/kg after oral administration.

On the basis of the found properties the compounds of formula 1 are suitable for the treatment of certain disorders and diseases which are related to disturbances in the central nervous system, in particular to disturbances of the serotonergic system.

The compounds are suitable, for example, for the treatment of psychoses, depressive states, anxiety, aggressive behaviour, sexual behaviour disturbances, memory disturbances, for example, those which occur with senile dementia and the Alzheimer syndrome, migraine, and with nausea and vomiting as a result of travelling disease. As stated hereinbefore, certain compounds are also suitable for the treatment of enhanced blood-pressure.

The compounds can be brought into a form suitable for humane application in the conventional manner, that is to say, formulated to compositions suitable for this purpose and to be preferably administered orally.

In view of their favourable properties, compounds of the general formula

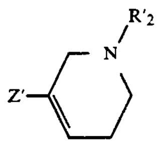

are prefered, wherein $R_2'$ is a hydrogen atom; a $C_1$-$C_4$ alkyl group substituted with 1-2 substituents selected from the group consisting of hydroxy, cyano, phenyl, substituted phenyl, phenoxy, substituted phenoxy, benzoyl and substituted benzoyl; or a group of the general formula

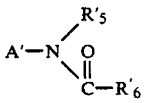

wherein

A' is an unbranched $C_2$-$C_4$ alkylene group;

$R_5'$ is a hydrogen atom or a methyl group; and $R_6'$ is an unsubstituted or substituted phenyl group; a saturated or unsaturated $C_1$-$C_{10}$ aliphatic or $C_4$-$C_{10}$ cycloaliphatic hydrocarbon group, or an unsubstituted or substituted phenyl($C_1$-$C_4$)alkyl group; or wherein $R_5'$ and $R_6'$, together with the carbamoyl group to which they are bound, form one of the ring systems of the formulas 20-26

20.
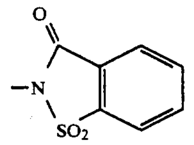

21.
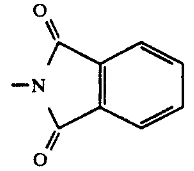

22.
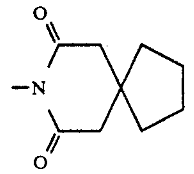

23.
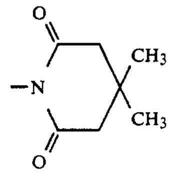

24.
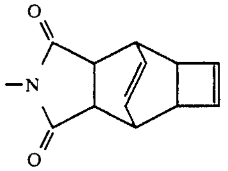

25.
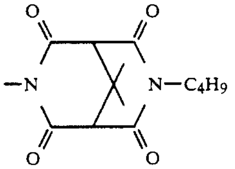

26.
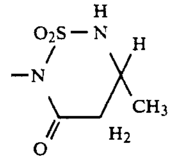

and

Z' is a group of the formula 2,3,4,6,7,8, 12 or 17 shown hereinbefore in claim 1, wherein $R_3$ is a hydrogen atom, a hydroxymethyl group, an esterified or etherified hydroxymethyl group, a methoxy group or an oxo function, $R_3'$ is a hydrogen atom and $R_4$ is a hydrogen atom or represents a chlorine atom, a methyl group or a methoxy group in the meta position with respect to the piperidine group;

as well as prodrugs and pharmaceutically acceptable salts hereof.

Compounds which are to be preferred in particular are:

(1) 3-(7-benzo[b]furanyl)-3,4-dehydropiperidine;
(2) 3-[7-(2,3-dihydrobenzo[b]furanyul)]-3,4-dehydropropiperidine;
(3) 3-(7-benzo[b]thienyl)-3,4-dehydropiperidine;
(4) 3-[5-(1,4-benzodioxanyl)]-3,4-dehydropiperidine;
(5) 3-[5-(1,4-benzodioxinyl)]-3,4-dehydropiperidine;
(6) 3-(1-naphthyl)-3,4-dehydropiperidine;
(7) 4-fluoro-N-[2-{3-(5-(1,4-benzodioxanyl))-3,4-dehydropiperidyl-1}ethyl]benzamide;
(8) 4-fluoro-N-[2-{3-(7-benzo[b]furanyl)-3,4-dehydropiperidyl-1}ethyl]benzamide;
(9) 4-fluoro-N-[2-{3-(7-(5-methoxybenzo[b]furanyl))-3,4-dehydropiperidyl-1}ethyl]benzamide.

and pharmaceutically acceptable salts of these compounds.

The new compounds according to the invention can be obtained in a manner known for the synthesis of analogous compounds.

The compounds may be prepared, for example, by reacting a compound of the general formula Z—Hal wherein Z has the meaning given hereinbefore and Hal is a halogen atom, with Mg of $R_7Li$, wherein $R_7$ is a $C_1$–$C_6$ alkyl group, and then reacting the resulting reaction product with a compound of the general formula

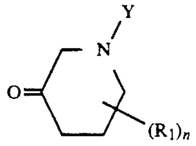

wherein $R_1$ and n have the meanings given hereinbefore, and

Y is an amino-protecting group or a branched or non-branched, saturated or unsaturated aliphatic hydrocarbon group having 1 to 4 carbon atoms.

The Grignard reaction with Mg is preferably carried out in a suitable anhydrous organic solvent, for example, an ether like diethyl ether, THF, or mixtures of these solvents. The reaction temperature usually is between room temperature and the boiling-point of the solvent used. The reaction with alkyl lithium, e.g., butyl lithium, is preferably carried out at reduced temperature in an anhydrous, inert organic solvent.

The 3,4-double bond in the piperidine ring is obtained by dehydration of the corresponding 3-hydroxypiperidine intermediate. Such 3-hydroxypiperidine compounds, having the general formula

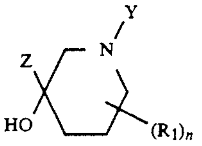

are new.

Suitable protective groups Y for the amino function are lower alkyl and benzyl. After removing said group Y in a manner known for this process, for example, by means of 1-chloroethyl chloroformiate, the resulting secondary amino function may be converted, if desired, in a subsequent reaction. Reaction with a compound of the general formula

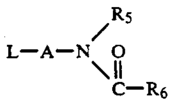

in which A, $R_5$ and $R_6$ have the meanings given hereinbefore and L is a suitable "leaving" group, for example, a mesylate group, a tosylate group or a halogen atom, provides a compound of the general formula 1 presented hereinbefore, wherein $R_2$ is a group of the general formula

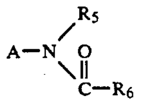

This latter reaction may be carried out both with and without an inert organic solvent. Suitable organic solvents are, for example, methyl ethyl ketone, dimethyl formamide, tetrahydrofuran, petroleum ether, alcohol and acetonitrile. In order to bind the releasing acid, and acid binding agent, for example, $NaHCO_3$ or $K_2CO_3$, or an organic base, for example, triethylamine, may be used. The reaction temperature usually is between room temperature and the boiling-point of the solvent used.

If a compound is to be prepared of the formula 1 shown hereinbefore, wherein $R_2$ is a group of the general formula

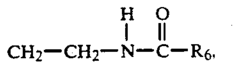

a compound of the general formula

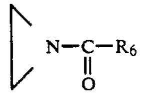

may also be used in the conversion of the above-mentioned secondary amino function. In this reaction the reaction components are preferably heated without a solvent at elevated temperature, preferably at approximately 100° C., for 1-6 hours. However, it is also possible to perform the last-mentioned reaction in an inert solvent, for example, acetone, methyl ethyl ketone or toluene, at a temperature between room temperature and the boiling-point of the solvent used.

The resulting secondary amino function may also be substituted by reaction with a suitable aldehyde, preferably in a polar organic solvent like an alcohol, followed by a reduction with a suitable reductant like sodium cyanoborohydride. Also a Mannich reaction is suitable for substituting said amino function. Then, under the usual Mannich conditions, the amino compound is reacted with formaldehyde or formaline and a suitable reactive compound like e.g. a pyrrole compound.

Furthermore, the compounds in which $R_3$ and/or $R_3'$ are/is a hydroxyalkyl group may be obtained by hydrolysis of the corresponding compound wherein $R_3$ and/or $R_3'$ respectively, are/is an esterified hydroxyalkyl group. Conversely, compounds in which $R_3$ is a hydroxyalkyl group may also be converted to final products in which $R_3$ is an esterified hydroxyalkyl group by esterification in a manner known per se.

Finally, the desired final products of formula 1, wherein the symbols have the meanings given above, may be obtained in that as the last reaction step one or more protective groups used for the protection of functional groups are removed or converted via methods conventionally used for this purpose.

The individual enantiomers of compounds of formula 1 may be obtained according to methods known per se, for example, by starting from optically active intermediate products, or by means of optically active reagents, or by separating a resulting racemate into the enantiomers by means of methods conventionally used for this purpose.

The invention will now be described in greater detail with reference to the ensuing specific examples.

EXAMPLE I

Preparation of 3-(1-naphthyl)-3,4-dehydropiperidine (6)

a) A solution of 31 g of 1-bromonaphthalene in 100 ml of dry tetrahydrofurane (THF) is added dropwise to 3,64 g of magnesium chips in 15 ml of dry THF; during addition the solution is gently refluxed. The reaction is carried out under nitrogen. After the addition is complete, the reaction mixture is refluxed for 1.5 h and then cooled down to ambient temperature. To this reaction mixture is then added dropwise a solution of 29.5 g of N-benzyl-3-piperidone in 100 ml of dry THF. After 3 h reflux and cooling, the reaction mixture is poured into a mixture of 150 ml of a 5% sodium bicarbonate solution and 150 ml of ethyl acetate. The water layer is washed twice with 100 ml ethyl acetate. The combined organic layers are dried and reduced to dryness. The residue is purified by column chromatography ($SiO_2$; $CH_2Cl_2$-methanol 98/2) The desired 1-(N-benzyl-3-hydroxypiperidyl-3)naphtalene is obtained in a yield of 25.6 g Alternatively the above reaction can be performed with n-butyllithium instead of magnesium: reaction temperature: −78° C.; addition of butyllithium in hexane.

b) The product obtained as described in a) can be dehydrated by dissolving it in 2-methoxyethanol, addition of conc. sulphuric acid and stirring at 50°-130° C. for a few hours. Also a good result is obtained by refluxing in conc. hydrochloric acid, if desiried after addition of dioxane. After cooling, the reaction mixture is made alkaline by adding 30% sodium hydroxide solution (ice cooling), after which the product is extracted with ethyl acetate, dried, evaporated and purified by column chromatography ($SiO_2$; $CH_2Cl_2$-methanol 98/2) The desired 1-(N-benzyl-3,4-dehydropiperidyl-3)naphthalene is obtained in a yield of 84%.

c) The protective benzyl group is removed as follows: The product obtained sub b) in a quantity of 10 g is dissolved in 100 ml of 1,2-dichloromethane, after which 4.5 ml of 1-chloroethyl chloroformiate are added under nitrogen. After refluxing for three hours, evaporating and separating the formed benzylchloride by means of column chromatography ($SiO_2$ as an adsorbent, $CH_2Cl_2$ as an eluent), 8.1 g of product are obtained. This product is refluxed for 2 hours in 150 ml of methanol and evaporated, after cooling. The residue is stirred with diethyl ether. The mono HCl-salt of the title compound (6) is obtained in a pure condition in a yield of 4.6 g; m.p. 251° C.

Alternatively, steps c) and d) may be carried out in the reversed sequence as follows:

To a solution of 3.4 g of 1-(N-benzyl-3-hydroxypiperidyl-3)naphthalene in 40 ml of methanol are added 0.15 g of 10% Pd/C and 2.7 g of ammonium formiate. Reflux for a few hours, cooling, filtration and evaporation. The residue is taken up into 200 ml of methoxyethanol and 15 ml conc.sulphuric acid. Heating at 120° C. for 2 hours, cooling, neutralizing ($Na_2CO_3$) and extraction with dichloromethane produces after drying and evaporating the desired 3-(1-naphthyl)-3,4-dehydropiperidine in a yield of 2.0 g.

EXAMPLE II

Preparation of 3-(7-benzo[b]furanyl)-3,4-dehydropiperidine (1)

a) 7-Bromobenzo[b]furan in a quantity of 15.2 g (79.2 mmol), dissolved in 100 ml of dry THF, is added dropwise to 1.9 g of magnesium (equimolar) in 25 ml of dry THF. The reaction mixture is refluxed for 2 hours, after which it is cooled to −20° C. A solution of 15 g (79.2 mmol) of N-benzyl-3-piperidone in 25 ml of dry THF is then added dropwise. After refluxing for 3 hours a part of the THF is evaporated, after which the residue is taken up in ethyl acetate, washed with 2N sodium hydroxide solution, dried and evaporated. The residue (25 g) is purified by column chromatography ($SiO_2$ as an adsorbent, $CH_2Cl_2/CH_3OH=96/4$ as an eluent). The desired 7-(N-benzyl-3-hydroxypiperidyl-3)benzo[b]furan is obtained in a yield of 16.8 g.

b) The product obtained according to a) in a quantity of 6.0 g (19.5 mmol) is dissolved in 100 ml of toluene and 4.1 g (21.4 mmol) of p-toluene sulphonic acid. The reaction mixture is boiled for 24 hours, water being collected. After cooling, the toluene solution is washed with 2N sodium hydroxide solution, dried and evaporated. The resulting 7-(N-benzyl-3,4-dehydropiperidyl-3)benzo[b]furan is obtained in a pure condition in a yield of 3.98 g after column chromatographic purification ($SiO_2$as an adsorbent, $CH_2Cl_2/CH_3OH=96/4$ as an eluent).

c) The product obtained according to b) is dissolved in a quantity of 6.9 g (23.8 mmol) into 150 ml of toluene, after which 3.87 g (24.7 mmol) of phenylchloroformiate are added. After refluxing for 6 hours the toluene solution is washed with 2N sodium hydroxide solution, dried and evaporated. Column chromatographic purification (ads. $SiO_2$, eluent: $CH_2Cl_2/CH_3OH=98/2$) provides the desired 7-(N-phenoxycarbonyl-3,4-dehydropiperidyl-3)benzo[b]furan in a yield of 6.4 g.

d) The product obtained according to c) is converted into a silyl ether by dissolving 6.3 g (19.7 mmol) in 150 ml of dry THF. 7.0 g (59 mmol) of trimethyl silyl ethanol are added to this solution under a nitrogen blanket at 0° C. After stirring for 10 minutes 6.6 g (59.1 mmol) of potassium tert.butoxide are added. The reaction mixture is again stirred for 16 hours, the temperature rising to room temperature. After the addition of a diethyl ether/THF mixture the reaction mixture is washed with 2N sodium hydroxide solution, dried and evaporated. 7-[N-(2-trimethylsilyl)ethoxycarbonyl-3,4-dehydropiperidyl-3]benzo[b]furan is obtained in a yield of 5.7 g.

e) Removal of the protective group is carried out as follows. 5.7 g (18.9 mmol) of the product obtained according to d) are dissolved in 100 ml of dry THF. 57 ml of 1 molar tetrabutyl ammonium fluoride in THF are added to this solution under nitrogen, after which the reaction mixture is stirred at room temperature for 70 hours. After evaporation, the residue is taken up in toluene and washed with 2N sodium hydroxide solution. The organic phase is separated and the aqueous phase is washed with a little methylene chloride. The combined organic phase is dried and evaporated. Column chromatographic purification (ads. $SiO_2$, eluent: $CH_2Cl_2/CH_3OH/NH_3=90/10/1$) provides the desired 3-(7-benzo[b]furanyl)-3,4-dehydropiperidine (1) in a yield of 1.9 g. The mono-HCl salt of (1) can be obtained by dissolving it in ethanol-hydrochloric acid and precipitation with diethyl ether; m.p. 224°-227° C.

EXAMPLE III

Dehydration by means of acetyl chloride in acetic acid.

A quantity of 13.3 g (41.2 mmol) of the 8-(N-benzyl-3-hydroxypiperidyl-3)benzodioxine-1,4 obtained from the Grignard reaction according to Example II a) is dissolved in 150 ml of acetic acid and 150 ml of acetyl chloride. The reaction mixture is refluxed at 85° C. for three hours. After evaporation under reduced pressure the residue is taken up in ethyl acetate, washed with 2N sodium hydroxide solution, dried and evaporated. Column chromatographic purification (ads. $SiO_2$, eluent acetone/hexane=1/9) provides the desired 8-(N-benzyl-3,4-dehydropiperidyl-3)benzodioxine-1,4 in a yield of 5.6 g.

EXAMPLE IV

Preparation of 4-fluoro-N-[2-{3-(7-benzo[b]furanyl)-3,4-dehydropiperidyl-1}ethyl]benzamide (8)

A quantity of 0.41 g (2 mmol) of the 3-(7-benzo[b]-furanyl)-3,4-dehydropiperidine prepared according to Example II are dissolved in 5 ml of dry toluene. 0.95 ml of a 36% solution (2 mmol) of 4-fluorobenzoyl-aziridine in toluene are added to this solution. After refluxing for 6 hours the reaction mixture is evaporated and the residue is purified by column chromatography (adsorbent $SiO_2$, eluent: $CH_2Cl_2/CH_3OH=98/2$).

The mono-HCl salt of the title compound is obtained in a yield of 0.25 g; m.p. 90°-93° C.

EXAMPLE V

Preparation of 5-methoxy-7-[N-{4-(N-saccharinyl)butyl}-3,4-dehydropiperidyl-3]benzo[b]furan (22)

A quantity of 0.77 g (2.9 mmol) of 3-[7-(5-methoxybenzo[b]furanyl]-3,4-dehydropiperidine obtained according to Example II together with 0.92 g (2.9 mmol) of N-(4-bromobutyl)saccharine, 2.5 ml of diisopropylamine and a few crystals of NaI are dissolved in 50 ml of acetonitrile. After refluxing for 24 hours the reaction mixture is evaporated. The residue is taken up in ethyl acetate, washed with sodium bicarbonate solution, dried and evaporated. After column chromatographic purification (ads. $SiO_2$, eluent: $CH_2Cl_2/CH_3OH/(C_2H_5)_3N=97/3/0.05$) the title compound is obtained in the form of the mono-HCl salt in a yield of 0.95 g; m.p. 146.5°-148.5° C.

EXAMPLE VI

Preparation of 2-[3-(7-benzo[b]furanyl)-3,4-dehydropiperidyl-1]-N-methyl-N-acetylethylamine (33)

3-(7-benzo[b]furanyl)-3,4-dehydropiperidine. HCl, obtained as described in Example II, in a quantity of 1.2 g, 1.1 g of N-acetyl-N-methyl-aminoacetaldehyde, 0.43 g of anhydrous sodium acetate and 0.25 ml of glacial acetic acid are dissolved in 35 ml of methanol. After stirring for 30 minutes at room temperature, this solution is cooled to $-5°$ C. and 0.34 g of sodium cyanoborohydride is added. After stirring for 20 hours at room temperature, the reaction mixture is evaporated to dryness and the residue is treated with 2N sodium hydroxide solution and extracted three times with 50 ml dichloromethane. After evaporation of the solvent the residue is purified by column chromatography ($SiO_2$;$CH_2Cl_2$-methanol-ammonia=98/1.5/0.5) With the aid of alcoholic HCl the product is converted into its HCl-salt.

The HCl-salt of the title compound is obtained in a yield of 720 mg. The molecular weight is determined by titration: found 344.9 (calc. 344.5).

EXAMPLE VII

Preparation of 2-[{3-(7-benzo[b]furanyl)-3,4-dehydropiperidyl-1}methyl]-5-(4-fluorophenyl)pyrrole (29)

The same starting compound as in Example VI, viz. 3-(7-benzo[b]furanyl)-3,4-dehydropiperidine.HCl, in a quantity of 1.18 g is together with 0.49 g sodium acetate suspended in 30 ml of abs. ethanol. Stirring for 30 min at room temperature; then 0.4 g of a 37% formaline solution in water is added. After again stirring for 30 min at room temperature, 0.89 g of 2-(4-fluorophenyl)pyrrole is added. After stirring for two hours at room temperature, the reaction mixture is poured into water and extracted with dichloromethane. Drying, evaporating and purification of the residue via column chromatography ($SiO_2$; petroleumether-ethylacetate 1/1) yields 1.4 g of the title compound; melting point 163° C.

According to one of the above methods the tabulated compounds are prepared. The table also includes the compounds mentioned in the Examples before.

TABLE

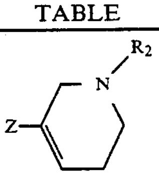

| Compd. no. | Prep. method Example | Z | $R_2$ | Salt | Physical data |
|---|---|---|---|---|---|
| 1 | II | 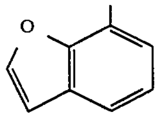 | H | HCl | m.p. 227° C. |
| 2 | II | 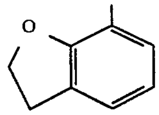 | H | HCl | m.p. 215° C. |
| 3 | I | 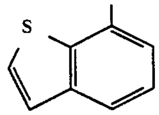 | H | HCl | m.p. 195° C. |
| 4 | I | 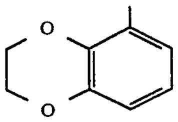 | H | HCl | m.p. 214° C. |
| 5 | II | 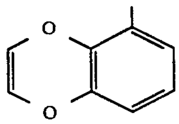 | H | HCl | m.p. 190° C. |
| 6 | I | 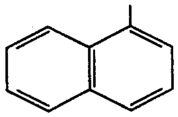 | H | HCl | m.p. 251° C. |

TABLE-continued
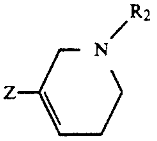
| Compd. no. | Prep. method Example | Z | $R_2$ | Salt | Physical data |
|---|---|---|---|---|---|
| 7 | IV | 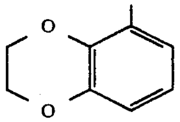 | 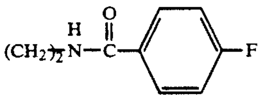 | HCl | m.p. 95° C. |
| 8 | IV | 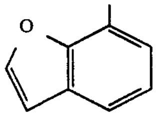 | " | HCl | m.p. 93° C. |
| 9 | IV | 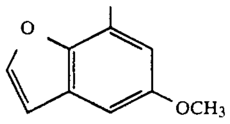 | 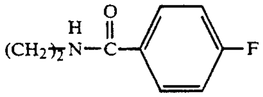 | HCl | m.p. 162° C. |
| 10 | I | 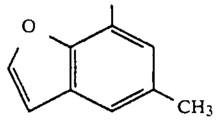 | H | HCl | m.p. 226° C. |
| 11 | I | 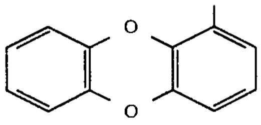 | H | HCl | m.p. 273° C. |
| 12 | III | 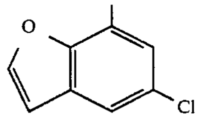 | H | HCl | m.p. 241° C. |
| 13 | I | 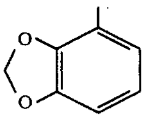 | H | fum* | m.p. 198° C. |
| 14 | II | 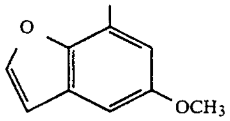 | H | HCl | m.p. 197° C. |
| 15 | V | 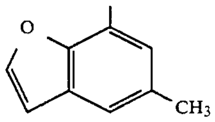 | 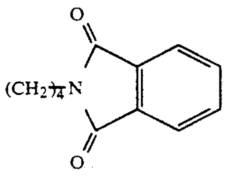 | HCl | m.p. 181° C. |

TABLE-continued
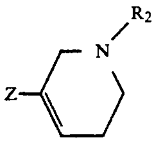
| Compd. no. | Prep. method Example | Z | R2 | Salt | Physical data |
|---|---|---|---|---|---|
| 16 | V | " | 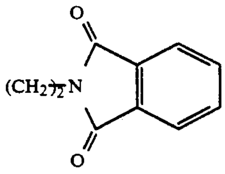 | HCl | m.p. 217° C. |
| 17 | V | " | 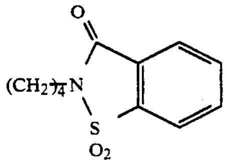 | HCl | m.p. 159° C. |
| 18 | V | 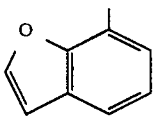 | 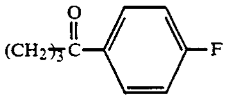 | HCl | m.p. 100° C. |
| 19 | IV | 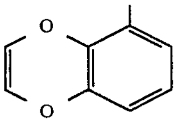 | 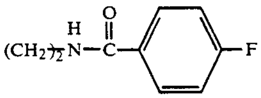 | — | MS:m/z = 380($M^+$) |
| 20 | V | 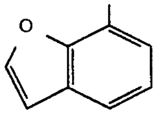 | 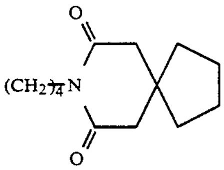 | fum* | m.p. 110° C. |
| 21 | V | " | 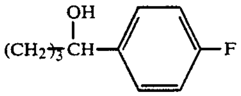 | HCl | m.p. 100° C. |
| 22 | V | 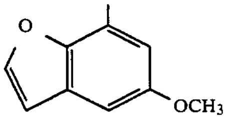 | 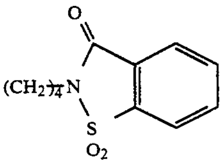 | HCl | m.p. 148° C. |
| 23 | IV | 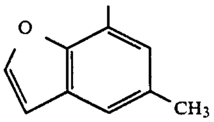 | 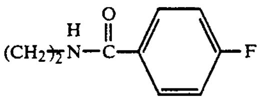 | fum* | m.p. 182° C. |
| 24 | V | 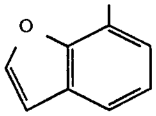 | $CH_2—CH_2OH$ | HCl | MS:m/z = 243($M^+$) |

TABLE-continued
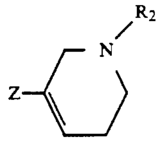
| Compd. no. | Prep. method Example | Z | $R_2$ | Salt | Physical data |
|---|---|---|---|---|---|
| 25 | V | 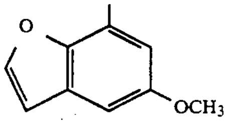 | 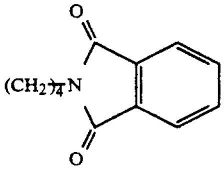 | HCl | m.p. 165° C. |
| 26 | V | 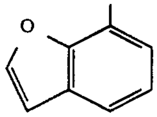 | 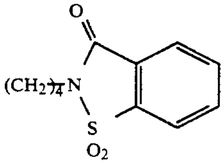 | HCl | MS:m/z = 436(M+) |
| 27 | VI | " | 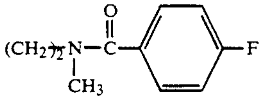 | HCl | MS:m/z = 378(M+) |
| 28 | VI | " | 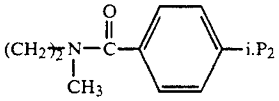 | mal* | m.p. 145° C. |
| 29 | VII | " | 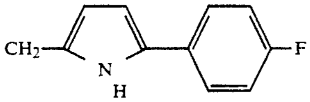 | mal* | m.p. 163° C. |
| 30 | V | 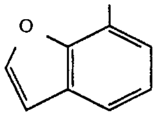 | $(CH_2)_3CN$ | HCl | m.p. 184° C. |
| 31 | V | " | 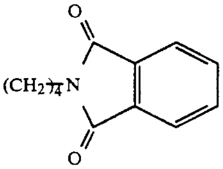 | HCl | m.p. 190° C. |
| 32 | V | " | 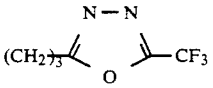 | HCl | m.p. 102° C. |
| 33 | VI | " | 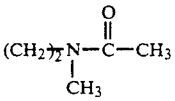 | HCl | MS:m/z = 298(M+) |
| 34 | V | " | 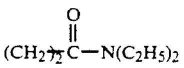 | — | MS:m/z = 326(M+) |

TABLE-continued
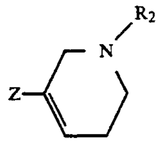
| Compd. no. | Prep. method Example | Z | $R_2$ | Salt | Physical data |
|---|---|---|---|---|---|
| 35 | V | 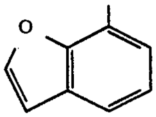 | 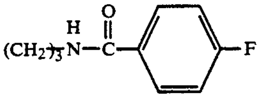 | HCl | MS:m/z = 378($M^+$) |
| 36 | V | ″ | 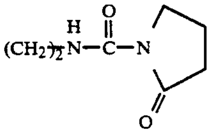 | HCl | MS:m/z = 353($M^+$) |
| 37 | V | ″ | n-$C_3H_7$ | HCl | m.p. 175° C. |
| 38 | V | ″ | 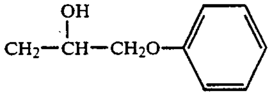 | HCl | m.p. 131° C. |
| 39 | V | ″ | 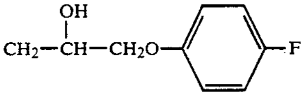 | HCl | m.p. 136° C. |
| 40 | V | 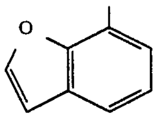 | n-$C_8H_{17}$ | HCl | m.p. 108° C. |
| 41 | V | ″ | 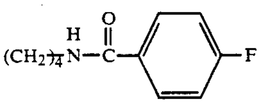 | fum* | m.p. 179° C. |
| 42 | VI | ″ | $CH_3$ | HCl | m.p. 180° C. |
| 43 | V | ″ | 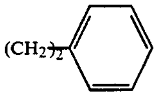 | HCl | m.p. 175° C. |
| 44 | IV | 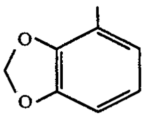 | 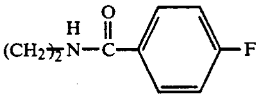 | fum* | MS:m/z = 368($M^+$) |
| 45 | V | 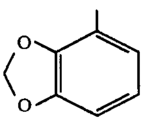 | 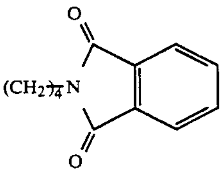 | HCl | m.p. 212° C. |

TABLE-continued
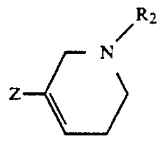
| Compd. no. | Prep. method Example | Z | $R_2$ | Salt | Physical data |
|---|---|---|---|---|---|
| 46 | V | " | 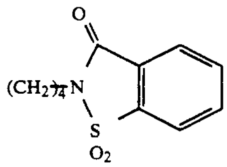 | HCl | MS:m/z = 440(M+) |
| 47 | V | 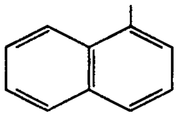 | " | HCl | MS:m/z = 446(M+) |
| 48 | IV | " | 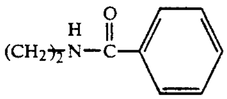 | HCl | MS:m/z = 356(M+) |
| 49 | IV | " | 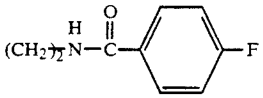 | HCl | MS:m/z = 374(M+) |
| 50 | I | 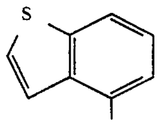 | H | HCl | m.p. 226° C. |
| 51 | IV | 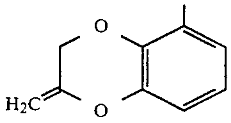 | 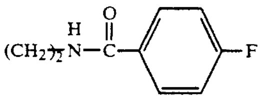 | HCl | MS:m/z = 394(M+) |
| 52 | IV | 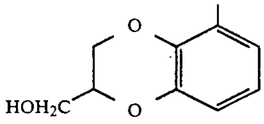 | " | HCl | MS:m/z = 412(M+) |
| 53 | IV | 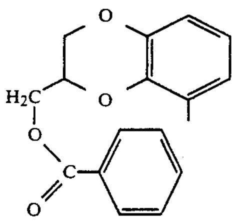 | " | HCl | MS:m/z = 516(M+) |
| 54 | IV | 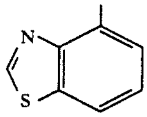 | " | HCl | MS:m/z = 380(M+) |

TABLE-continued
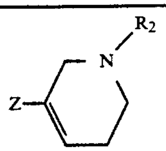
| Compd. no. | Prep. method Example | Z | $R_2$ | Salt | Physical data |
|---|---|---|---|---|---|
| 55 | I | 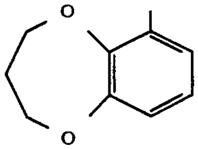 | H | fum* | MS:m/z= 231($M^+$) |
| 56 | V | " | 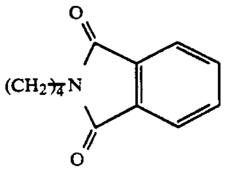 | HCl | m.p. 125° C. |
| 57 | IV | 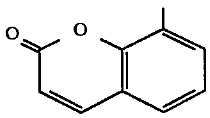 | 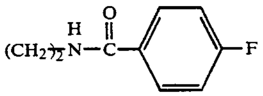 | HCl | MS:m/z = 392($M^+$) |
| 58 | IV | 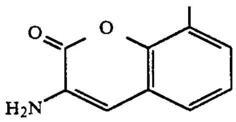 | " | HCl | MS:m/z = 407($M^+$) |
| 59 | IV | 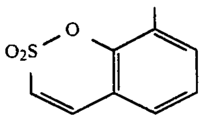 | " | HCl | MS:m/z = 428($M^+$) |
| 60 | IV | 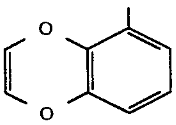 | 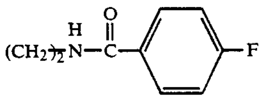 | HCl | MS:m/z = 380($M^+$) |
| 61 | V | 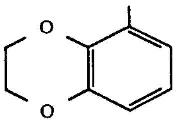 | 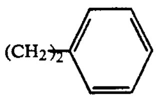 | HCl | MS:m/z = 321($M^+$) |
| 62 | VII | " | 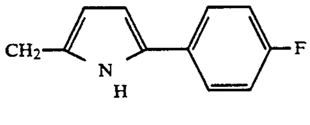 | — | MS:m/z = 390($M^+$) |
| 63 | VI | " | $CH_3$ | HCl | MS:m/z = 231($M^+$) |
remarks:
*fum = fumarate
mal = maleinate
What is claimed is:
1. A 3,4-dehydropiperidine derivative of the formula (1)

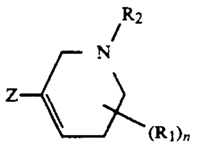

(1)

wherein $R_1$ is a hydrogen atom or an alkyl group having 1-3 carbon atoms;

wherein $R_2$ represents a group of the formula

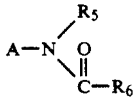

wherein

A is a branched or non-branched alkylene group having 2 to 10 carbon atoms, $R_5$ is a hydrogen atom or an alkyl group having 1 to 3 carbon atoms, and $R_6$ is an unsubstituted or substituted aryl or heteroaryl group, said heteroaryl group being selected from thienyl, furyl, pyridyl, quinolyl, pyrimidyl, imidazolyl, pyrrolyl, oxadiazolyl, pyrazinyl and indolyl, wherein the substituents are selected from the group consisting of halogen, $C_1$–$C_4$ alkyl, $C_1$–$C_4$ alkoxy, hydroxy, esterified or etherified hydroxy, trifluoromethyl, alkylcarbonyl, cyano, $C_1$–$C_4$ alkylamino and di($C_1$–$C_4$)alkylamino; a saturated or unsaturated $C_1$–$C_{10}$ aliphatic or $C_4$–$C_{10}$ cycloaliphatic hydrocarbon group; an unsubstituted or substituted aralkyl group substituted with halogen, $C_1$–$C_4$ alkyl, $C_1$–$C_4$ alkoxy, hydroxy, trifluoromethyl, alkylcarbonyl, cyano, $C_1$–$C_4$ alkylamino or di($C_1$–$C_4$) alkylamino; or a heterocyclic ring system selected from the group consisting of tetrahydrofuryl, tetrahydropyranyl, piperidyl and pyrrolidinyl which may be substituted with one or more substituents selected from the group consisting of $C_1$–$C_4$ alkyl, oxo and halogen;

n has the value 1 or 2; and

Z is one of the groups of the formulas 15 or 16 with the proviso that group 15 may be bound to the piperidine group via position 4 or 7 and the group 17 may be bound to the piperidine group via the indicated position in which groups $R_3$ and $R_3'$ may be equal or different and represent hydrogen atoms; halogen atoms; oxo functions; saturated or unsaturated $C_1$–$C_{10}$ aliphatic hydrocarbon groups; $C_1$–$C_6$ hydroxyalkyl groups; esterified or etherified $C_1$–$C_6$ hydroxyalkyl groups, wherein the ester group is derived from benzoic acid, from benzoic acid substituted with one or more equal or different substituents selected from the group consisting of halogen, $C_1$–$C_4$ alkyl, $C_1$–$C_4$ alkoxy, hydroxy, esterified or etherified hydroxy, trifluoromethyl, alkylcarbonyl, cyano, $C_1$–$C_4$ alkylamino and di($C_1$–$C_4$)alkylamino, or from a straight or branched $C_2$–$C_8$ aliphatic carboxylic acid, and wherein the ether group is a straight or branched, saturated or unsaturated aliphatic $C_1$–$C_8$ hydrocarbyloxy group, a $C_3$–$C_6$ cycloalkoxy group or a ($C_3$–$C_6$ cycloalkyl)$C_1$–$C_4$ alkoxy group; $C_1$–$C_4$ alkylcarbonyl groups; hydroxy groups; amino groups; $C_1$–$C_3$ alkylamino groups; di($C_1$–$C_3$)alkylamino groups; substituted or non-substituted aryl groups or heteroaryl groups, said heteroaryl groups being selected from thienyl, furyl, pyridyl, quinolyl, pyrimidyl, imidazolyl, pyrrolyl, oxadiazolyl, pyrazinyl and indolyl, wherein the substituents are selected from the group consisting of halogen, $C_1$–$C_4$ alkyl, $C_1$–$C_4$ alkoxy, hydroxy, esterified or etherified hydroxy, trifluoromethyl, alkylcarbonyl, cyano, $C_1$–$C_4$ alkylamino and di($C_1$–$C_4$)alkylamino; or aryl($C_1$–$C_3$)alkyl groups; and $R_4$ is a hydrogen atom, a halogen atom, a cyano group, a hydroxy group, a trifluoromethyl group, an alkyl group, an alkoxy group, an alkylthio group, an alkanoylamino group, an alkanoyl group, an aminocarbonyl group, an N-alkylaminocarbonyl group, an N,N-dialkylaminocarbonyl group, an alkanoyloxy group or an alkoxycarbonyl group, wherein the alkyl groups have 1 to 10 carbon atoms;

or a pharmaceutically acceptable salt thereof.

2. A compound as claimed in claim 1, characterized in that the symbols in the formula 1 have the meanings given in claim 1, with the proviso that (i) the substituent $R_4$ in the group Z is a hydrogen atom or a fluorine atom and (ii) the meaning of $R_5$ in substituent $R_2$ is hydrogen.

3. A compound as claimed in claim 1, of the formula

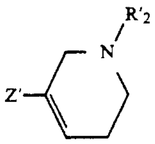

wherein $R_2'$ is a group of the formula

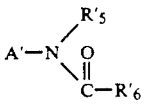

wherein

A′ is an unbranched $C_2$–$C_4$ alkylene group;

$R_5'$ is a hydrogen atom or a methyl group; and $R_6'$ is an unsubstituted or substituted phenyl group; a saturated or unsaturated $C_1$–$C_{10}$ aliphatic or $C_4$–$C_{10}$ cycloaliphatic hydrocarbon group, or an unsubstituted or substituted phenyl($C_1$–$C_4$)alkyl group;

and

Z′ is a group of the formula 17 shown hereinbefore in claim 1, wherein $R_3$ is a hydrogen atom, a hydroxymethyl group, of a methoxy group, $R_3'$ is a hydrogen atom and $R_4$ is a hydrogen atom or a chlorine atom, a methyl group or a methoxy group in the meta position with respect to the piperidine group;

or a pharmaceutically acceptable salt thereof.

4. A pharmaceutical composition which comprises a 3,4-dehydropiperidine derivative as the active substance, characterized in that the composition comprises at least one compound as claimed in claim 1 plus a pharmaceutically acceptable carrier.

5. A pharmaceutical composition which comprises a 3,4-dehydropiperidine derivative as the active substance, characterized in that it comprises at least one compound as claimed in claim 2 as the active ingredient plus a pharmaceutically acceptable carrier.

6. A pharmaceutical composition which comprises a 3,4-dehydropiperidine derivative as the active substance, characterized in that it comprises at least one compound as claimed in claim 3 as the active ingredient plus a pharmaceutically acceptable carrier.

7. A method of treating disorders or diseases which are related to disturbances of the central nervous system in the body of a warm-blooded living being by administering to the being a composition as claimed in claim 5 in quantity sufficient for a psychotropic effect.

8. A method of treating elevated blood pressure in the body of a warm-blooded living being by administering to the being a composition as claimed in claim 5 in an effective quantity.

* * * * *

UNITED STATES PATENT AND TRADEMARK OFFICE
CERTIFICATE OF CORRECTION

PATENT NO. : 5,296,497

DATED : March 22, 1994

INVENTOR(S) : Jan HARTOG, et al

It is certified that error appears in the above-identified patent and that said Letters Patent is hereby corrected as shown below:

Column 3, line 25, correct formula 14 to read as follows:

-- 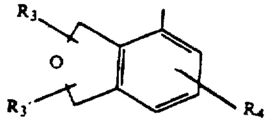 14. --

Column 3, line 30, correct formula 15 to read as follows:

-- 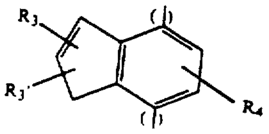 15. --

UNITED STATES PATENT AND TRADEMARK OFFICE
CERTIFICATE OF CORRECTION

PATENT NO. : 5,296,497

DATED : March 22, 1994

INVENTOR(S) : Jan HARTOG, et al

It is certified that error appears in the above-identified patent and that said Letters Patent is hereby corrected as shown below:

Column 27, line 43, "n has the value 1 or 2;" should be deleted.

Column 27, line 44, "16" should read --17--; and before "with" the following formulas should be inserted:

-- 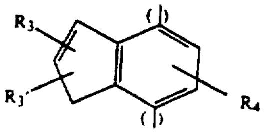 15. 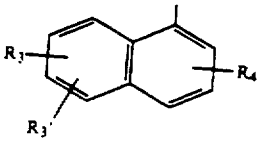 17. --

Column 30, line 2, "5" should read --4--.

Signed and Sealed this

Sixth Day of June, 1995

Attest:

BRUCE LEHMAN

Attesting Officer

Commissioner of Patents and Trademarks